US008614074B2

(12) United States Patent
Taran et al.

(10) Patent No.: US 8,614,074 B2
(45) Date of Patent: Dec. 24, 2013

(54) PROCESS FOR PRODUCING ISOMER ENRICHED CONJUGATED LINOLEIC ACID COMPOSITIONS

(75) Inventors: Victoria Taran, Wormerveer (NL); Krishnadath Bhaggan, Wormerveer (NL); Jeroen Monster, Wormerveer (NL)

(73) Assignee: Stepan Specialty Products, LLC, Wilmington, DE (US)

( * ) Notice: Subject to any disclaimer, the term of this patent is extended or adjusted under 35 U.S.C. 154(b) by 723 days.

(21) Appl. No.: 12/296,603

(22) PCT Filed: Apr. 4, 2007

(86) PCT No.: PCT/EP2007/003059
§ 371 (c)(1),
(2), (4) Date: Apr. 16, 2009

(87) PCT Pub. No.: WO2007/118614
PCT Pub. Date: Oct. 25, 2007

(65) Prior Publication Data

US 2009/0246840 A1 Oct. 1, 2009

(30) Foreign Application Priority Data

Apr. 13, 2006 (EP) .................................... 06252054

(51) Int. Cl.

| | |
|---|---|
| ***C12P 7/64*** | (2006.01) |
| ***C07C 57/00*** | (2006.01) |
| ***C11C 3/00*** | (2006.01) |
| ***C07C 53/00*** | (2006.01) |

(52) U.S. Cl.
USPC ............ 435/134; 554/224; 554/167; 554/221

(58) Field of Classification Search
None
See application file for complete search history.

(56) References Cited

U.S. PATENT DOCUMENTS

| | | | | |
|---|---|---|---|---|
| 5,892,074 | A | 4/1999 | Seidel | 554/126 |
| 6,153,774 | A | 11/2000 | Seidel | 554/193 |
| 6,225,486 | B1 | 5/2001 | Saebo et al. | 554/221 |
| 6,420,557 | B1 | 7/2002 | Harris et al. | 544/262 |
| 2001/0018453 | A1 | 8/2001 | Seidel | 514/547 |
| 2001/0025113 | A1 | 9/2001 | Saebo et al. | 554/223 |
| 2001/0049451 | A1 | 12/2001 | Seidel | 554/127 |
| 2003/0130533 | A1* | 7/2003 | Yamauchi et al. | 554/122 |
| 2004/0122094 | A1 | 6/2004 | Saebo et al. | 514/547 |

FOREIGN PATENT DOCUMENTS

| | | | | |
|---|---|---|---|---|
| EP | 0902082 A1 | 3/1999 | | A23D 9/00 |
| EP | 1 801 193 | 6/2007 | | C11C 1/08 |
| WO | WO 97/18320 A1 | 5/1997 | | A23D 9/00 |
| WO | WO 03/043792 A1 | 5/2003 | | B28B 7/24 |
| WO | WO 03/043972 A2 | 5/2003 | | A23D 9/00 |
| WO | WO 2005/087017 A2 | 9/2005 | | |

OTHER PUBLICATIONS

Kim, S.-J. et al., "Preparation of a Large Quantity of *cis*-9,*trans*-11 and *trans*-10,*cis*-12 Conjugated Linoleic Acid (CLA) Isomers from Synthetic CLA", J. Food Sci. Nutr., 5(2);96-92 (2000).

Chin et al., "Dietary sources of conjugated dienoic isomers of linoleic acid, a newly recognized class of anticarcinogens", Journal of Food Composition and Analysis, 5:185-197 (1992).

Jain et al., "Photocatalytic production and processing of conjugated linoleic rich soy oil", J. Agric. Food Chem., 54:5590-5596 (2006).

Kim et al., "A simple method for the preparation of highly pure conjugated linoleic acid (CLA) synthesized from safflower seed oil", J. Food Sci. Nutr. 5(1):10-14 (2000).

Nagao et al., "Fractionation and enrichment of CLA isomers by selective esterification with *Candida rugosa* lipase", Journal of the American Oil Chemists' Society, 79(3):303-308(2002).

Scholfield et al., "A Simple Method for preparation of Methyl trans-10,cis-12 Octadecadienoate", Journal of the American Oil Chemists' Society, 47(8):303 (1970).

Sehat et al., "Improved Separation of Conjugated Fatty Acid Methyl Esters by Silver-Ion High-Performance Liquid Chromatography", Lipids, 34(4):407-413 (1999).

Berdeaux et al., "A Simple Method of Preparation of Methyl *trans*-10,*cis*-12- and *cis*-9,*trans*11-Octadecadienoates from Methyl Linoleate", JAOCS, 75(12):1740-1755 (2003).

Kim Y.-J. et al., "Selective Increase in Conjugated Linoleic Acid in Milk Fat by Crystallization", Journal of Food Science, 64(5):792-795 (1999).

Park et al., "Evidence That the *trans*-10,*cis*-12 Isomer of Conjugated Linoleic Acid Induces Body Composition Changes in Mice", Lipids, 34(3):235-241 (1999).

Haas et al., "Lipase-Catalyzed Fractionation of Conjugated Linoleic Acid Isomers", Lipids, 34(9):979-987 (1999).

Watanabe et al., "Production of MAG of CLA in a Solvent-Free System at Low Temperature with *Candida rugosa* Lipase", JAOCS, 80(9):909-914 (2003).

Warwel et al., "Substrate selectivity of lipases in the esterification of *cis/trans*-isomers and positional isomers of conjugated linoleic acid (CLA)", Biotechnology Letters, 22:1151-1155 (2000).

(Continued)

*Primary Examiner* — Anne Gussow
*Assistant Examiner* — Channing S Mahatan
(74) *Attorney, Agent, or Firm* — Barnes & Thornburg LLP; Brian R. Dorn

(57) ABSTRACT

A process for the preparation of a composition comprising the cis9, trans11 and trans10, cis12 isomers of conjugated linoleic acid (CLA) comprises: providing a mixture comprising cis9, trans11 and trans10, cis12 isomers of conjugated linoleic acid (CLA) in which one of the cis9, trans11 and trans10, cis12 isomers is present in a first weight ratio X of at least 1.3:1 with respect to the other isomer; and subjecting the mixture to crystallization to form a composition comprising the cis9, trans11 and trans10, cis12 isomers in which one of the cis9, trans11 and trans10, cis12 isomers is present at a second weight ratio Y with respect to the other isomer, wherein Y is greater than X.

8 Claims, No Drawings

(56) References Cited

OTHER PUBLICATIONS

Yamauchi-Sato et al., "Fractionation of Conjugated Linoleic Acid Isomers by Selective Hydrolysis with *Candida rugosa* Lipase", J. Oleo Sci., 52(7):367-374 (2003).

Scholfield et al., "A Simple Method for Preparation of Methyl *trans*-10, *cis*-12 Octadecadienoate", JAOCS, 47(8):303 (1970).

Berdeaux et al., "A Simple Method for Preparation of Methyl *trans*-10, *cis*-12 and *cis*-9, *trans-11*-Octadecadienoates from Methyl Linoleate", JAOCS, 75(12):1749-1755 (1998).

* cited by examiner

PROCESS FOR PRODUCING ISOMER ENRICHED CONJUGATED LINOLEIC ACID COMPOSITIONS

This invention relates to a process for producing a composition. In particular, the invention relates to a process for producing a composition comprising the cis9, trans11 and trans10, cis12 isomers of conjugated linoleic acid (CLA), which is enriched in one of the isomers compared to the other.

The beneficial effects of conjugated long chain polyunsaturated fatty acids, such as CLA, in food products for animals or humans has long been recognised. CLA is a conjugated dienoic fatty acid having 18 carbon atoms. As a result of the presence of the two double bonds in CLA, geometrical isomerism is possible and the CLA molecule or moiety may exist in a number of isomeric forms. The cis9, trans11 ("c9t11") and trans10, cis12 ("t10c12") isomers of CLA are generally the most abundant and beneficial pharmacological effects have been identified for each of these isomers.

Since the amount of cis9, trans11 and trans10, cis12 isomers in chemically synthesised CLA mixtures is generally around equimolar, there is a need for processes which allow the purification of the isomers or enrichment of the mixtures in one of these isomers. CLA mixtures enriched in one of the isomers may have advantageous pharmacological effects, particularly since the pharmacological effect of one isomer may be very different from that of the other isomer.

WO 97/18320 describes a process for the preparation of materials with a high content of long chain polyunsaturated fatty acids. The process involves the use of an enzyme which has the ability to discriminate between different geometrical isomers.

Nagao et al, JAOCS, volume 79, no 3, (2002), pages 303 to 308 describes the fractionation and enrichment of CLA isomers by selective esterification with *Candida rugosa* lipase. Lauryl alcohol is used to form the esters.

The lipase-catalysed fractionation of conjugated linoleic acid isomers is described in Haas et al, Lipids, Volume 34, no 9, (1999), pages 979 to 987. The process is carried out on a small scale and the document concludes that enzyme-catalysed esterification rather than hydrolysis is more practical.

US 20010025113 describes isomer enriched CLA compositions. In one of the examples, an enriched isomer mixture is obtained by crystallisation of a mixture of ethyl esters from a 1:1 isomer mixture produced after conjugation. The method requires very low temperatures below −57° C.

U.S. Pat. No. 6,420,577 discloses a method for the commercial preparation of CLA. Crystallisation is used to purify the CLA but there is no separation of different isomers.

Berdeaux et al., JAOCS, Volume 75, no 12 (1998), pages 1749-1755 and Kim et al., J. Food Sci. Nutr, Volume 5, no 2 (2000), pages 86-92 disclose a method for the preparation of conjugated isomers of linoleic acid involving the separation and purification of the methyl esters of alkali-isomerised methyl linoleate.

Kim et al., J. Food Sci. Nutr, Volume 5, no 1 (2000), pages 10-14 discloses a method for the preparation of highly pure CLA chemically-synthesized from safflower oil (SSO).

WO 2005/087017 discloses processes for synthesising compositions enriched in the cis10, trans12 isomer of CLA and compositions enriched in the trans9, cis11 isomer of CLA.

Although processes for producing CLA isomer mixtures are known, there can be difficulties in increasing the amount of one isomer to relatively high levels. For example, the processes that rely on the selectivity of a lipase for one isomer compared to another isomer require the reaction not to proceed to completion and there is, therefore, a compromise between yield and the degree of isomer enrichment. There remains a need for a process for preparing CLA isomer mixtures that are enriched in one isomer, which can give a relatively high yield and/or a relatively high content of one isomer relative to other isomers and which can be carried out relatively inexpensively on a relatively large scale, for example without the need for very low temperatures (e.g., below −57° C.).

The separation of CLA isomers is generally carried out with the CLA isomers in the form of esters. The reason for this is thought to be due to the larger difference in the melting point of the esters compared to the free acids. This greater difference in melting point makes the esters easier to separate than the free acids by crystallisation. Indeed, the separation of the isomers of the corresponding free acids has been described in the literature as almost impossible (see, for example, US 2001/0018453). Also, Jain et al, J. Agric, Food Chem, Volume 54 (2006), pages 5590-5596 describes the inseparability of the isomers as limiting their commercial utility. However, separation of the esters may require the additional step of forming esters from the free acids and this can be costly and time consuming. Thus, there remains a particular need for a process for preparing CLA isomer mixtures that are enriched in one isomer which can overcome these problems.

According to the invention, there is provided a process for the preparation of a composition comprising the cis9, trans 11 and trans 10, c is 12 isomers of conjugated linoleic acid (CLA), which comprises:

providing a mixture comprising cis9, trans 11 and trans10, cis12 isomers of conjugated linoleic acid (CLA) in which one of the cis9, trans11 and trans10, cis12 isomers is present in a first weight ratio X of at least 1.3:1 with respect to the other isomer; and subjecting the mixture to crystallisation to form a composition comprising the cis9, trans11 and trans10, cis12 isomers in which one of the cis9, trans 11 and trans10, cis12 isomers is present at a second weight ratio Y with respect to the other isomer, wherein Y is greater than X.

The process of the invention has been found to allow the production of compositions containing relatively high amounts of the cis9, trans11 or the trans10, cis12 isomer, preferably the cis9, trans11 isomer, in a good yield.

Surprisingly, it has been found that a mixture comprising the free acids of cis9, trans11 and trans10, cis12 isomers of CLA may be separated by subjecting the mixture to a crystallisation step according to the invention, despite the two isomers having very similar melting points.

Moreover, by adjusting the ratio of the isomers before crystallisation, it has surprisingly been found that it is possible to separate the different isomers as free acids by crystallisation, at a higher temperature than would be required, for example, for the crystallisation of the corresponding esters.

Preferably, the crystallisation is carried out in the presence of a solvent. Suitable solvents comprise a polar organic compound. More preferred solvents comprise a C3 to C6 ketone, a C1 to C6 alcohol, water or a mixture thereof. The most preferred solvent is acetone, either alone or in admixture with one or more other solvents such as water, but in which acetone is the major component of the solvent (i.e., in which acetone is present in an amount of at least 55%, more preferably at least 70%, even more preferably at least 90%, by weight). The crystallisation is preferably carried out in the substantial absence or the complete absence of urea. For example, urea is preferably present in an amount of less than 5% by weight of the solvent, more preferably less than 3% by weight, such as less than 1% by weight, e.g., less than 0.5% by weight, less than 0.1% by weight or even 0% by weight.

The crystallisation step that forms part of the process of the invention is carried out using a suitable amount of solvent to effect selective crystallisation. It has been found to be particularly preferred to employ a weight ratio of solvent to total cis9, trans11 and trans10, cis12 isomers that is in the range of from about 20:1 to about 1:1, such as about 10:1 to about 1:1, more preferably from about 9:1 to about 2:1, even more preferably from about 8:1 to about 2:1, such as from about 6:1 to about 5:2 or from about 5:1 to about 3:1. The use of a ratio of about 4:1 is particularly preferred. Working at these levels of solvent allows the most effective selective crystallisation at a temperature in the range of about −15° C. to −35° C. When the ratio of solvent to total cis9, trans11 and trans10, cis12 isomers is less than about 1.5:1, it has been found that the selectivity of the process is greatly reduced.

The conditions for the crystallisation step are selected to allow effective and selective separation of the cis9, trans11 and trans10, cis12 isomers. The preferred temperature at which the crystallisation is carried out is a temperature below 0° C., more preferably a temperature in the range of from −10 to −40° C., such as −15 to −35° C., for example −18 to −30° C.

In one embodiment of the invention, the crystallisation step is carried out in the absence of mechanical stirring. The crystallisation may be carried out essentially quiescently i.e., with only convection currents providing movement in the mixture.

The crystallisation may be effected by controlled cooling or by sudden ("crash") cooling, typically starting at room temperature. Controlled cooling may take place for up to 72 hours and may involve cooling over a period of 2 to 24 hours at a rate of about 1 to 5° C. per hour. Crash cooling may take place in less than 5 hours, more preferably less than 2 hours or less than 1 hour, even more preferably less than 30 minutes such as less than 15 minutes or less than 5 minutes. Both cooling methods may be followed by keeping the cooled mixture and solvent at the low temperature for up to 48 hours e.g., up to 60 hours.

The invention comprises the step of providing a mixture in which one of the cis9, trans11 and trans10, cis12 isomers is present in a first weight ratio X of at least 1.3:1 with respect to the other isomer (although other ratios, such as 1.1:1, 1.15:1 and 1.2:1, are possible). It has been found that this first step of ensuring inequality of the amount of the two isomers allows more effective and/or selective crystallisation to be carried out. The mixture can be provided in a number of different ways. Typically, the mixture is formed by treatment of a composition comprising the cis9, trans11 and trans10, cis12 isomers in roughly equal molar amounts. However, the mixture may be provided in other ways.

Preferably, the mixture is provided by a process comprising the step of treating a composition comprising the cis9, trans11 and trans10, cis12 isomers with an enzyme that exhibits greater selectivity for one of the isomers than the other isomer. Typically, the enzyme is a lipase.

In one embodiment, the mixture may be provided by at least partially esterifying a composition comprising conjugated linoleic acid with an enzyme that is selective for the cis9, trans 11 isomer compared to the trans10, cis12 isomer to form an ester fraction enriched in the cis9, trans11 isomer compared to the trans10, cis12 isomer and hydrolysing the ester fraction to form the free acid.

In another embodiment, the mixture may be provided by at least partially esterifying a composition comprising conjugated linoleic acid with at least one monohydric alcohol having from 1 to 5 carbon atoms to obtain the corresponding conjugated linoleic acid esters and selectively hydrolysing at least a proportion of the esters with an enzyme to produce alcohol, free fatty acids enriched in the c9t11 isomer and CLA esters enriched in the t10c12 isomer, with removal of at least part of the alcohol formed.

Starting compositions for providing the mixture are preferably CLA compositions comprising roughly equimolar amounts of the cis9, trans11 and trans10, cis12 isomers, such as can be obtained by chemical synthesis of CLA, such as by conjugation of linoleic acid, as described in EP-A-0902082, for example.

Preferably, one, more than one or all of the esterification and hydrolysis steps are carried out using a lipase. The most preferred lipases are those exhibiting selectivity for either the cis9, trans11 or the trans10, cis12 isomer compared to the other isomer. Examples of suitable lipases are those from *Candida rugosa* or *Geotrichum candidum*. However, it is only necessary that one of the esterification or hydrolysis steps exhibits selectivity for one of the isomers and the other esterification or hydrolysis steps may be non-selective and may involve non-selective chemical or enzymatic reactions.

Preferably, the first ratio X is at least about 1.3 to 1, such as at least about 1.4:1 or at least about 1.5:1. Preferably, the first ratio X does not exceed about 4:1 and more preferably is less than about 3:1 or less than about 2:1, such as less than 1.8:1, for practical reasons.

The crystallisation step is carried out so as to increase the relative proportion of one of the isomers compared to the other isomer. The weight ratio of the isomers after the crystallisation step is a second ratio Y. Y is greater than X and is typically greater than about 1.5:1, more preferably greater than about 1.7:1, such as greater than about 2:1, for example at least about 3:1 or at least about 4:1 or at least about 5:1 or even at least about 10:1. Y is usually not more than about 20:1, more preferably not more than about 50:1 or about 100:1.

The process of the invention may comprise further steps. For example, the process preferably comprises the step of separating the composition after the crystallisation step, optionally washing the composition and optionally drying the composition. However, preferably the composition is not washed. It is also preferred that the composition is allowed to dry by removal of the solvent to the atmosphere without any external heating, either at ambient pressure or under reduced pressure. The composition typically forms the crystalline product and may be separated from the liquor (i.e., the liquid remaining after crystallisation) by filtration or centrifugation, for example.

The composition may be subjected to one or more further crystallisation steps, as described herein, in order to increase the value of Y even further.

The process may comprise a step of forming an ester from the composition. Suitable esters include alkyl esters derived from alcohols having from 1 to 6 carbon atoms. Glycerides (including mono-, di- and triglycerides and mixtures thereof) are particularly preferred. The esters can be formed by esterification (for example using an enzyme; a selective enzyme may further increase the isomer ratio Y) and are optionally purified, for example by distillation.

The process of the invention may be carried out to increase the amount of either the cis9, trans11 or the trans10, cis12 isomer in the final composition. Preferably, the composition comprises the cis9, trans11 isomer in an amount greater than the trans10, cis12 isomer. In another embodiment, the composition comprises the trans10, cis12 isomer in an amount greater than the cis9, trans11 isomer.

The composition produced in the process of the invention preferably comprises at least 60% by weight of compounds containing the cis9, trans11 isomer, more preferably at least 70% by weight of compounds containing said isomer, based on the total amount of the C18:2 fatty acid compounds in the composition. Alternatively, the composition comprises at least 60% by weight of compounds containing the trans10, cis12 isomer, more preferably at least 70% by weight of compounds containing said isomer, based on the total amount of the C18:2 fatty acid compounds in the composition The composition produced in the process of the invention may be used in a food product, food supplement or pharmaceutical product. Therefore, the invention also contemplates a food product, food supplement or pharmaceutical product comprising a composition of the invention. Food supplements or pharmaceutical products may be in the form of capsules or other forms, suitable for enteral or parenteral application, and comprise a composition of the invention.

Food supplements (which term includes nutritional supplements) are particularly preferred. Examples of food supplements include products in the form of a soft gel or a hard capsule comprising an encapsulating material selected from the group consisting of gelatin, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the unit dosage of conjugated fatty acid in the food supplements is from 1 mg to 1000 mg (more preferably from 100 mg to 750 mg).

Food products optionally comprise the composition as a blend with a complementary fat. The blend may comprise 0.3-95 wt %, preferably 2-80 wt %, most preferably 5-40 wt % of the product of the invention and 99.7-5 wt %, preferably 98-20 wt %, most preferably 95-60 wt % of a complementary fat selected from: cocoa butter, cocoa butter equivalents, palm oil or fractions thereof, palm kernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils.

The food products (which term includes animal feed), may contain a fat phase, wherein the fat phase contains the product of the invention. Examples of suitable food products include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, creams, cream alternatives, dry soups, sauces, drinks, cereal bars, sauces, snack bars, dairy products, bakery products, clinical nutrition products and infant food or infant formulations.

Pharmaceutical products include pharmaceutical compositions, such as in the form of tablets, pills, capsules, caplets, multiparticulates including: granules, beads, pellets and micro-encapsulated particles; powders, elixirs, syrups, suspensions and solutions. Pharmaceutical compositions will comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions and syrups. Optionally, the compositions comprise one or more flavouring and/or colouring agents.

Pharmaceutically acceptable carriers suitable for use in such compositions are well known in the art of pharmacy. The compositions of the invention may contain 0.1-99% by weight of conjugated fatty acid. The compositions are generally prepared in unit dosage form. Preferably the unit dosage of conjugated fatty acid is from 1 mg to 1000 mg (more preferably from 100 mg to 750 mg). The excipients used in the preparation of these compositions can include excipients known in the art.

The following non-limiting examples illustrate the present invention. In the examples and throughout this specification, all percentages are percentages by weight unless otherwise indicated.

EXAMPLES

Example 1

Preparation of Starting Material with Ratio X for Fractionation

Conjugated linoleic acid (CLA) mixture having an equimolar ratio of the two isomers cis9, trans11 (c9,t11) and trans10, cis12 (t10,c12) was prepared as described in U.S. Pat. No. 6,160,140 Examples 1 and 2.

The obtained free fatty acids from this process were esterified with an alcohol. The esterification reaction was catalyzed by a lipase. In this example, glycerol was used as the alcohol and the reaction was catalysed by Lipozyme RM IM. Thereafter, the obtained glycerides were partially hydrolysed and the acid fraction was separated from the glyceride fraction by means of distillation.

About 400 kg fully refined glyceride product was partially hydrolysed. The reaction was catalysed by lipase from *Candida rugosa*. After distillation at 170-190° C., a distillate fraction was obtained with a ratio of the two isomers c9,t11 and t10,c12 of X=~2.9.

Example 2

Enrichment of c9,t11 CLA Isomer Via Wet Fractionation

General Method

CLA free fatty acids (CLA-FFA) with a ratio of the two isomers c9,t11 and t10,c12 of X were dissolved in a solvent in a 500 ml glass vessel. The obtained solution was put in the freezer at −30° C. and was statically cooled down for 48 hours. After this, the formed crystals were filtered using a Buchner funnel under reduced pressure.

The obtained stearin (solid, crystalline) fraction was melted up to ambient and the remaining solvent was evaporated by means of rotor evaporation. The yield was calculated according to the following formula:

$$\text{Yield}[\%] = \frac{[CLA-FFA]_{stearin}(g)}{[CLA-FFA]_{start}(g)} * 100$$

The ratio of the two isomers c9,t11 and t10,c12 in the stearin (solid) and olein (liquid; liquor after crystallisation) fractions was calculated from the fatty acid composition measured by standard FAME GLC method:

$$\text{ratio}[Y] = \frac{[c9,\ t11CLA]}{[t10,\ c12CLA]} : \frac{[t10,\ c12CLA]}{[t10,\ c12CLA]}$$

Static Wet Fractionation

A series of four experiments was carried out using different oil to solvent ratios. The ratio (X) of the two isomers c9,t11 and t10,c12 in the starting material was 2.6, while the solvent used was acetone. The oil to solvent ratio investigated was 1:1.5, 1:2.3, 1:4 and 1:9. The obtained results are shown in Table 1.

TABLE 1

Fatty acid composition of the stearin fraction and yield obtained after wet fractionation at −30° C.

| | | Ratio oil:solvent | | | |
|---|---|---|---|---|---|
| | | 1:1.5 | 1:2.3 | 1:4 | 1:9 |
| | Starting | Yield [%] | | | |
| Description | material | 77.7 | 62.3 | 49.6 | 6.2 |
| C16:0 | 4.2 | 4.6 | 5.1 | 6.2 | 12.6 |
| C18:0 | 1.4 | 1.7 | 2.0 | 2.4 | 5.5 |
| CLA TT | 1.3 | 1.2 | 1 | 0.9 | 0.7 |
| C18:2 c9, t11 | 0.6 | 0.5 | 0.4 | 0.3 | 0.2 |
| C18:2 t10, c12 | 0.5 | 0.5 | 0.5 | 0.4 | 0.3 |
| C18:2 11, 13 | 2.1 | 1.8 | 1.5 | 1.2 | 0.6 |
| C18: 1 C | 14.1 | 14.0 | 14.2 | 13.9 | 11.3 |
| CLA OX | 0.2 | 0.3 | 0.2 | 0.3 | 0.2 |

TABLE 1-continued

Fatty acid composition of the stearin fraction and yield obtained after wet fractionation at −30° C.

| | | Ratio oil:solvent | | | |
|---|---|---|---|---|---|
| | | 1:1.5 | 1:2.3 | 1:4 | 1:9 |
| | Starting | Yield [%] | | | |
| Description | material | 77.7 | 62.3 | 49.6 | 6.2 |
| C18:2T | 0.6 | 0.3 | 0.3 | 0.2 | 0.1 |
| C18:2C | 1.3 | 1.0 | 0.9 | 0.7 | 0.4 |
| TTnc | 0.6 | 0.4 | 0.3 | 0.3 | 0.2 |
| C20:0 | 0.1 | 0.2 | 0.2 | 0.2 | 0.6 |
| C22:0 | 0.1 | 0.1 | 0.2 | 0.2 | 0.3 |
| C18:2 C9, T11 | 52.8 | 57.6 | 61.9 | 63.9 | 62.4 |
| C18:2 T10C12 | 20.4 | 15.8 | 11.3 | 8.7 | 4.4 |
| Total CLA isomers | 78.0 | 77.7 | 76.8 | 75.7 | 68.7 |
| unidentified | 1.0 | 1.2 | 1.9 | 1.1 | 0.9 |
| Ratio X | 2.6 | — | — | — | — |
| Ratio Y | — | 3.6 | 5.5 | 7.4 | 14.2 |

Example 3

Influence of Controlled Cooling on Enrichment of c9t11 CLA Isomer Via Wet Fractionation General Method CLA-FFA with a ratio of the two isomers c9,t11 and t10,c12 of X was dissolved in a solvent in a small scale crystalliser. The crystalliser consists of a jacketed 1-L glass vessel provided with a filtration unit at the bottom. The vessel is connected to a temperature control unit in order to be able to use a controlled temperature cooling program. The obtained solution was statically cooled down for 48 hours.

The obtained stearin fraction was melted up to ambient and the remaining solvent was evaporated by means of rotor evaporation. The yield and the ratio of the two isomers c9,t11 and t10,c12 was calculated according to above mentioned formulae.

Controlled Cooling Fractionation

Two experiments were carried out. In one experiment, oil/solvent mixture was cooled down according to a temperature cooling program, while in the second experiment crash cooling was applied. The ratio (X) of the two isomers c9,t11 and t10,c12 in the starting material was 7.6. The oil to solvent ratio used was 1:4.

The following temperature cooling program was investigated:

From 20° C. to −10° C. in 2 hours

From −10° C. to −15° C. in 1 hour

From −15° C. to −25° C. in 2 hours

The mixture was left at −25° C. for 24 hours; after this the temperature was decreased further to −27° C. The mixture was filtered after 48 hours.

The crash cooling experiment was carried out according to Example 2. The obtained results are shown in Table 2.

TABLE 2

Fatty acid composition of the stearin fraction and yield obtained after wet fractionation for 48 hours.

| | | Ratio oil:solvent | |
|---|---|---|---|
| | | 1:4 | 1:4 |
| | | Yield (%) | |
| | | 20.8 | 73.01 |
| Description | Starting material | Controlled cooling | crash cooling |
| C16:0 | 4.4 | 7.4 | 5.5 |
| C18:0 | 0.7 | 1.4 | 0.9 |
| CLA TT | 0.6 | 0.8 | 0.4 |
| C18:2 c9, t11 | 0.3 | 0.3 | 0.2 |
| C18:2 t10, c12 | 0.2 | 0.1 | 0.1 |
| C18:2 11, 13 | 3.0 | 1.9 | 0.9 |
| C18:1 C | 13.4 | 12.8 | 11.8 |
| CLA OX | 0.2 | 0.2 | 0.2 |
| C18:2T | 0.5 | 0.3 | 0.2 |
| C18:2C | 1.7 | 1.2 | 0.7 |
| TTnc | — | 0.4 | 0.2 |
| C20:0 | — | 0.1 | — |
| C18:2 C9, T11 | 65.8 | 68.0 | 76.6 |
| C18:2 T10C12 | 8.7 | 5.1 | 2.4 |
| Total CLA isomers | 78.8 | 76.4 | 80.7 |
| unidentified | 0.2 | — | — |
| Ratio X | 7.6 | — | — |
| Ratio Y | — | 13.1 | 31.3 |

Example 4

Influence of Ratio X in Starting Material on Enrichment (Comparative; X has to be Greater than 1)

One experiment was carried out according to the procedure described in Example 1. Starting material with two different ratio of the two isomers (X=1 and X=1.5) was investigated. The oil to solvent ratio used was 1:4 and the mixture was crystallised at −28° C. for 24 and 48 hours. The obtained results are shown Table 3.

TABLE 3

Fatty acid composition of the stearin fraction and yield obtained after wet fractionation of material with X = 1 and X = 1.5.

| | Ratio X | | | |
|---|---|---|---|---|
| | 1 | | 1.5 | |
| | Crystallisation time [hrs] | | | |
| | 24 | 48 | 24 | 48 |
| | Stearine Yield [%] | | | |
| Description | 38.4 | 51.9 | 38.8 | 50.5 |
| C16:0 | 7.6 | 7.7 | 7.9 | 8.6 |
| C18:0 | 4.5 | 4.4 | 3.9 | 4.1 |
| CLA TT | 0.6 | 0.6 | 0.6 | 0.6 |
| C18:2 c9, t11 | 0.4 | 0.4 | 0.3 | 0.3 |
| C18:2 t10, c12 | 0.3 | 0.3 | 0.4 | 0.3 |
| C18:2 11, 13 | 0.4 | 0.3 | 0.6 | 0.5 |
| C18:1 C | 9.1 | 8.9 | 11.4 | 11.3 |
| CLA OX | 0.1 | 0.2 | 0.2 | 0.2 |
| C18:2T | 0.2 | 0.2 | 0.2 | 0.2 |
| C18:2C | 0.3 | 0.4 | 0.6 | 0.5 |
| TTnc | 0.3 | 0.3 | 0.3 | 0.3 |
| C20:0 | 0.7 | 0.7 | 0.6 | 0.6 |
| C22:0 | 0.5 | 0.5 | 0.4 | 0.4 |
| C18:2 C9, T11 | 42.2 | 42.4 | 56.8 | 57.9 |
| C18:2 T10C12 | 32.8 | 32.8 | 15.7 | 14.1 |
| Total CLA isomers | 76.8 | 77.0 | 74.7 | 73.9 |
| unidentified | — | — | 0.1 | 0.1 |
| Ratio Y | 1.3 | 1.3 | 3.6 | 4.1 |

Oil to solvent ratio is 1:4.

Example 5

The physical/chemical characteristics of pure c9, t11 and t10, c12 conjugated linoleic acid (CLA FFA) and c9, t11 and t10, c12 conjugated linoleic acid methyl esters (CLA ME) are as follows:

| CLA isomer | Melting point, ° C. [a] | | Boiling point,° C. (760 Torr) [b] | | Vapor pressure, Torr [b] | |
|---|---|---|---|---|---|---|
| c9, t11 FFA | 10.1 | Δ = 4.2 | 381.6 | Δ = 3.9 | 7.01E−7 | Δ = 2.53E−7 |
| t10, c12 FFA | 14.3 | | 377.7 | | 9.54E−7 | |
| c9, t11 ME | −37.6 | Δ = 16.5 | 378.5 | Δ = 36 | 6.26E−6 | Δ = 6.25E−6 |
| t10, c12 ME | −21.1 | | 414.5 | | 1.32E−8 | |

[a] Measured on Perkin Elmer Pyris I DSC, with liquid nitrogen cooling. The purity of the isomers was: c9, t11 CLA isomer 98%, t10, c12 CLA isomer 97%.

[b] Calculated using Advanced Chemistry Development (ACD/Labs) Software V8.14 for Solaris, SciFinder

The invention claimed is:

1. A process for the preparation of a composition comprising the cis9, trans11 and trans10, cis12 isomers of conjugated linoleic acid (CLA), which comprises:

providing a mixture comprising the free acids of cis9, trans11 and trans10, cis12 isomers of conjugated linoleic acid (CLA) in which one of the cis9, trans11 and trans 10, cis12 isomers is present in a first weight ratio X of from 1.3:1 to 4:1 with respect to the other isomer;

subjecting the mixture to a crystallization step to form a composition comprising the cis9, trans11 and trans10, cis12 isomers in which one of the cis9, trans11 and trans10, cis12 isomers is present at a second weight ratio Y with respect to the other isomer, wherein Y is greater than X, wherein the composition comprises at least 60% by weight of the cis9, trans11 isomer or the trans10, cis12 isomer, based on the total amount of C18:2 fatty acids in the composition, wherein the mixture is provided by at least partially esterifying a composition comprising CLA with an enzyme that is selective for the cis9, trans11 isomer compared to the trans10, cis12 isomer to form an ester fraction enriched in the cis9, trans11 isomer compared to the trans10, cis12 isomer and a free acid fraction enriched in the trans10, cis12 isomer compared to the cis9, trans11 isomer and separating the ester fraction and the free fatty acid fraction.

2. The process as claimed in claim 1, further comprising hydrolyzing the ester fraction to form a free acid composition enriched in the cis9, trans11 isomer compared to the trans10, cis12 isomer.

3. The process as claimed in claim 1, wherein the mixture is provided by at least partially esterifying a composition comprising conjugated linoleic acid with at least one monohydric alcohol having from 1 to 5 carbon atoms to obtain the corresponding conjugated linoleic acid esters and selectively hydrolyzing at least a proportion of the esters with an enzyme to produce alcohol, free fatty acids enriched in the cis9, trans11 isomer and CLA esters enriched in the trans10, cis12 isomer, with removal of at least part of the alcohol formed, and separating the free fatty acids from the CLA esters.

4. The process as claimed in claim 1, wherein the enzyme is a lipase.

5. The process of claim 4, wherein the lipase is a *Candida rugosa* lipase or a *Geotrichum candidum* lipase.

6. The process of claim 1, wherein the crystallization is effected by controlled cooling.

7. The process of claim 1, wherein the crystallization is effected by sudden cooling.

8. The process of claim 7, wherein the sudden cooling starts at room temperature.

* * * * *